United States Patent
Davis et al.

(10) Patent No.: US 10,156,569 B2
(45) Date of Patent: Dec. 18, 2018

(54) RAPID TEST TO DETERMINE THE NECESSITY OF REVACCINATION

(71) Applicant: Kansas State University Research Foundation, Manhattan, KS (US)

(72) Inventors: Rolan Davis, Manhattan, KS (US); Michael Moore, St. George, KS (US)

(73) Assignee: KANSAS STATE UNIVERSITY RESEARCH FOUNDATION, Manhattan, KS (US)

( * ) Notice: Subject to any disclaimer, the term of this patent is extended or adjusted under 35 U.S.C. 154(b) by 12 days.

(21) Appl. No.: 15/504,489

(22) PCT Filed: Aug. 18, 2015

(86) PCT No.: PCT/US2015/045620
§ 371 (c)(1),
(2) Date: Feb. 16, 2017

(87) PCT Pub. No.: WO2016/028733
PCT Pub. Date: Feb. 25, 2016

(65) Prior Publication Data
US 2017/0234876 A1    Aug. 17, 2017

Related U.S. Application Data

(60) Provisional application No. 62/097,351, filed on Dec. 29, 2014, provisional application No. 62/038,578, filed on Aug. 18, 2014.

(51) Int. Cl.
| | | |
|---|---|---|
| G01N 33/569 | (2006.01) |
| G01N 33/558 | (2006.01) |
| G01N 33/53 | (2006.01) |
| G01N 33/537 | (2006.01) |

(52) U.S. Cl.
CPC ....... *G01N 33/56983* (2013.01); *G01N 33/53* (2013.01); *G01N 33/537* (2013.01); *G01N 33/558* (2013.01); *G01N 33/569* (2013.01)

(58) Field of Classification Search
None
See application file for complete search history.

(56) References Cited

U.S. PATENT DOCUMENTS

| | | |
|---|---|---|
| 2003/0040021 A1 | 2/2003 | Clark et al. |
| 2012/0237923 A1 | 9/2012 | Guo et al. |
| 2013/0101987 A1 | 4/2013 | O'Conner et al. |

FOREIGN PATENT DOCUMENTS

| | | |
|---|---|---|
| WO | 1999040438 | 8/1999 |

OTHER PUBLICATIONS

Orciari et al. (Vaccine. 2001; 19: 4511-4518).*
International Search Report and Written Opinion dated Nov. 23, 2015, in PCT/US2015/045620, filed Aug. 18, 2015.

* cited by examiner

*Primary Examiner* — Shanon A. Foley
(74) *Attorney, Agent, or Firm* — Hovey Williams LLP (57) ABSTRACT

Rapid, point of care semi-quantitative tests for viral or bacterial antibody titer, and methods and kits for carrying out the same. The test article comprises a first elongated solid support with a sample application region and a detection region. The detection region comprises immobilized antigen that specifically binds a minimum immunoprotective level of antibody to at least one pathogen of interest. Depending upon the test results, the assay can rapidly indicate whether the animal has the presumptive minimally-protective level of antibody to the target pathogen, or needs to be re-vaccinated.

30 Claims, 2 Drawing Sheets

RAPID TEST TO DETERMINE THE NECESSITY OF REVACCINATION

CROSS-REFERENCE TO RELATED APPLICATIONS

The present application is the National Stage of international Patent Application No. PCT/US2015/045620 filed Aug. 18, 2015, which claims the priority benefit of U.S. Provisional Patent Application Ser. No. 62/038,578, filed Aug. 18, 2014, and Ser. No. 62/097,351, filed Dec. 29, 2014, each entitled RAPID TEST TO DETERMINE THE NECESSITY OF REVACCINATION, and incorporated by reference in its entirety herein.

BACKGROUND OF THE INVENTION

Field of the Invention

The present invention relates to rapid, point of care semi-quantitative assays for viral or bacterial antibody titer to determine need for vaccination.

Description of Related Art

Current practice generally provides that humans and animals be vaccinated against certain diseases on a set schedule (e.g., every one or three years) without regard to existing antibodies. However, there is a recognized risk of continued vaccination against rabies, as well as other viral disease agents. Limiting the number of vaccinations needed, based on titer determinations, would likely decrease an individual's chance of vaccine reactions as well as vaccine associated sarcomas This approach would recognize a One Health approach by harmonizing the approaches between animals and humans.

SUMMARY OF THE INVENTION

The present invention is broadly concerned with methods for determining the necessity of re-vaccination of an animal against at least one pathogen. The method comprises contacting a test sample from the animal with a test article comprising a first elongated solid support having a top surface. The top surface comprises a sample application region and a detection region, with the sample application region being in capillary flow communication with the detection region and having a first path of flow therebetween. The detection region comprises first immobilized antigen and a soluble dye in a first defined area of the detection region, wherein the immobilized antigen specifically binds a minimum immunoprotective level of antibody to the at least one pathogen. The detection region also comprises a control compound in a second defined area of the detection region, where this second defined area being distinct from the first defined area. In the method, the test sample is deposited on the sample application region, and test sample flows by capillary action to the detection region along the first path of flow. The detection region is observed for disappearance of the soluble dye from the first defined area of the detection region. Next, the detection region is contacted with reporter antibodies labelled to generate a detectable signal. The reporter antibodies are configured to selectively bind the first immobilized antigen and non-selectively bind the control compound. The detection region is again observed for changes. The changes comprise appearance of a detectable signal in the second defined area as a positive control (i.e., confirming a valid test result). Other changes that may be detected in the detection region include the appearance of a detectable signal in the first defined region. Appearance of a detectable signal in the first defined area indicates that the animal does not have the minimum immunoprotective level of antibody to the at least one pathogen, such that there is a need for re-vaccination of the animal. However, absence of a detectable signal in the first defined area indicates that the animal has the minimum immunoprotective level of antibody to the at least one pathogen such that there is no necessity for re-vaccination of the animal.

Test articles for determining the necessity of re-vaccination of an animal against at least one pathogen are also described herein. The test article a first elongated solid support having a top surface. The top surface comprises a sample application region and a detection region, with the sample application region being in capillary flow communication with the detection region and having a first path of flow therebetween. The detection region comprises first immobilized antigen and a soluble dye in a first defined area of the detection region, wherein the immobilized antigen specifically binds a minimum immunoprotective level of antibody to the at least one pathogen. The detection region also comprises a control compound in a second defined area of the detection region, where this second defined area being distinct from the first defined area. The test article also comprise a second elongated solid support. The second solid support intersects the first solid support at the detection region. The top surface of the second solid support comprises a reporter application region. The top surface of the second solid support is coplanar with the top surface of the first solid support, such that the reporter application region is in capillary flow communication with the detection region defining a second path of flow therebetween.

Also described herein is a kit for point-of-care determination of the necessity of re-vaccination of an animal against a pathogen. The kit comprises a test article according to any of the embodiments described herein, along with instructions for use. For example, instructions may include the protocol for collecting a test sample from the animal and testing the test sample using the test article to determine if the animal has a minimum immunoprotective level of antibody against the pathogen such that there is no necessity for re-vaccination of the animal. Optional reagents and/or buffers for use in the assay can also be included with the kit.

The present methods and devices are particularly suited for screening animals, including humans, for minimum immunoprotective levels of anti-rabies antibodies.

BRIEF DESCRIPTION OF THE DRAWINGS

Figure (FIG. 1 is a graph showing the comparison of two populations (current and out of date dogs) by modelling their reverse cumulative distributions with respect to the observed titer. At a fixed titer value, this can be thought of as the proportion of animals in the population with a titer value at least as large as the given titer.

DETAILED DESCRIPTION

The present invention is concerned with a semi-quantitative, rapid viral (or bacterial) antibody titer test. In one embodiment of the invention the antibody titer test comprises one or more antigens with a known concentration, and which are known to bind to a pre-determined level of antibody. Also provided herein is a method of making a determination of a titer above a standard level that is recognized as immunoprotective. The test allows in-clinic testing and allows boosters to be given to animals and humans only when indicated by a low antibody response. All pathogens, diseases, or conditions that animals (including humans) are routinely vaccinated against could be developed using this methodology. Examples in companion animals would include titers against rabies, as well as canine distemper virus (CDV), canine parvovirus, and canine adenovirus, type 2 (CAD-2) in dogs and feline panleukopenia virus (FPV), feline herpesvirus-2 (FHV-1), feline calicivirus (FCV) and rabies virus in cats.

The current standard for humans that may become exposed to rabies virus is that they have titers checked every two years following initial vaccination. A routine booster dose is only recommended for patients when the serum titer falls below 0.5 IU/ml. Currently titer of rabies antibodies in vaccinated animals and humans is performed by a serum neutralization method. This testing is performed only in laboratories capable of performing high complexity testing (CLIA standards) as well as those willing to handle live rabies virus cultures. This requires that all personnel are vaccinated against rabies.

According to the American Animal Hospital Association (AAHA), core vaccinations for dogs include immunization against CDV, canine parvovirus, type 2-(CPV-2), CAD-2, and rabies virus. Core vaccinations for cats include FPV, FHV-1, FCV, and rabies virus. Vaccines for viral diseases of domestic dogs and cats have a rather long duration of immunity, but this period is variable within a population. As well, it is recognized for at least with CDV and CPV-2, there are animals that do not initially seroconvert to these vaccines, leading to lack of protection. This shows that there would be utility in being able to individually test animals for the need to booster doses of core vaccines.

Similarly in humans, vaccines for a variety of diseases, such as for tetanus, measles and hepatitis, are given at recommended intervals without any determination as to whether a vaccination is in fact needed.

We propose the use of rapid test technology such as lateral flow device (LF) or Dual Path Platform (DPP) testing to be applied to semi-quantitative detection of antibodies against one or more diseases. More specifically, the test would set the amount of antigen in the detector line as appropriate for the specific disease of interest. If the detector line is completely bound by patient antibodies and the reporter antibodies cannot bind, this would indicate a titer above pre-established levels and the vaccine (booster) could be withheld. Recommended titers that indicate adequate vaccination are as follows:

Canine: CDV ($\geq 1:16$), CPV ($\geq 1:40$), CAV-2 ($\geq 1:16$) and rabies ($\geq 1:50$)

Feline: FPV ($\geq 1:20$), FHV-1 ($\geq 1:16$), FCV ($\geq 1:16$) and rabies ($\geq 1:50$)

For example, a titer level at or above 0.5 IU/mL of rabies antibodies is considered immunoprotective and vaccination is contra indicated. Inclusion of a viral antigen line that binds 0.5 IU/ml in a patient's sera, would allow for screening of patients with rabies antibody titers above that level.

This method could test for antibodies against several antigens at the same time. This method will allow for quick testing without using live viral (or bacterial) cultures and still allow a semi-quantitative antibody titer. Development of a rapid test specific to rabies would allow for testing by those not vaccinated against rabies.

Rapid test devices allow point of care diagnostics for animal and human health provider. Allowing bench top testing would allow determination of the necessity of booster vaccination during a routine office visit due to ease of testing. As well, costs of a rapid test are expected to be lower than traditional methods of rabies antibody titers.

Any currently known, or future developed, rapid test platform can be used, including for example the technology present in various lateral flow (LF) devices, as well as more recently developed Dual Path Platform devices that have two independent flow paths for the sample and conjugate (e.g., DPP® available for ChemBio Diagnostic Systems, U.S. Pat. No. 7,189,522, incorporated by reference herein).

In one or more embodiments, the test article comprises a first elongated solid support having a top surface. In general, the top surface comprises a sample application region and a detection region. The sample application region is in capillary flow communication with the detection region whereby material absorbed on the solid support may flow by capillary action from the sample application region to the detection region. Accordingly, there is a region on the top surface between the sample application region and the detection region that defines a first path of flow of the material. The elongated solid support can be a test strip or ribbon (with two terminal ends) or other suitable geometric shape to facilitate flow of the material from the sample application region to the detection region. Any sorbent material (or combination of sorbent materials) can be used for the solid support, as long as it is capable of absorbing, either by capillary action or otherwise, molecules that pass through/along the solid support. The top surface of the solid support will typically be substantially planar or flat, so as not to impede the flow or the test sample, and a porous membrane matrix with a suitable thickness that allows flow through of the test sample (liquid). Cellulose-based materials are particularly suited for use as test strips. In one or more embodiments, the elongated solid support comprises a nitrocellulose membrane covered by an absorbent pad (sample application region) at or near one end and a wicking pad at or near the other end, with the detection region being positioned therebetween. Thus, the sample, after being applied to the sample application region, wicks up the nitrocellulose membrane, causing the fluid to pass over the detection region as it is "pulled" towards the wicking pad. Other suitable material for the membrane include nylon, paper, polymers (e.g., polyester, polystyrene, polyacrylamide), and activated forms thereof.

The detection region comprises immobilized antigen of a first type and a soluble dye in a first defined area of the detection region. The detection region contains an amount of immobilized antigen capable of binding to an amount of antibody corresponding to a minimum immunoprotective level of the antibody against the designated pathogen. Thus, the phrase "minimum immunoprotective level of antibody" refers to the level of antibody (antibody titer) in the circulation of the patient animal at which there is a presumptive protection against the designated pathogen. As such, if an animal is identified as having this minimum immunoprotective level of antibody, (re)vaccination is unnecessary and in some cases contra indicated. The term pathogen is used herein to designate any viral or bacterial organism, or other disease or condition, against which animals can be vaccinated. Reference to the antigen being "immobilized" in the first defined area of the detection region means that the antigen is stably bound to the solid support (e.g., through covalent attachment or otherwise to confer permanent or semi-permanent attachment) so that it will remain affixed at a stationary location (designated as the first defined area) and will not be washed away by flowing sample. It will be appreciated that regardless of how the antigen is immobilized in the detection region, it must nevertheless retain its antigenicity towards its corresponding antibodies.

The term "antigen" is used herein to refer to any substance that has antigenicity for the corresponding anti-pathogen antibodies. Thus, exemplary antigens include whole/intact pathogens, surface proteins, fragments, and the like, which contain at least the immunoreactive portion of the pathogen. In preferred embodiments, whole, killed pathogens are used. For example, heat-resistant antigens can be prepared from viral strains by boiling of a washed and concentrated viral culture. The boiled suspension is centrifuged to remove cell debris, and the supernatant containing the antigen is filtered. The antigen of interest along with a soluble dye can be deposited as a first defined area of the detection region. The antigen and dye can be arranged in various configurations to define the first defined area. For example, the first defined area can be in the shape of a line or a dot. Reference here to a "soluble dye" includes any substance with a detectable signal (e.g., color visible in the visual spectrum) that can be deposited with the antigen, but which will be readily washed away by the flowing sample. It will be appreciated that the soluble dye is used as a marker to indicate that the test sample fluid has passed over the antigen defined area, and completion of the first step of the inventive assays.

The detection region also comprises a control compound in a second defined area of the detection region. The second defined area is separate and distinct from the first defined area. In other words, although the first and second defined areas may be next to one another (laterally) in the detection region, they should not touch or overlap. The control compound can be arranged in various configurations on the solid support to define the second defined area. For example, the second defined area can be in the shape of a line or a dot. Like the antigen, the control compound will be immobilized in the second defined area of the detection region so that it is stably bound to the solid support (e.g., through covalent attachment or otherwise to confer permanent or semi-permanent attachment) so that it will remain affixed at a stationary location (designated as the second defined area) and will not be washed away by flowing sample. It will be appreciated that regardless of how the control compound is immobilized in the detection region, it must nevertheless retain its binding activity towards the reporter antibodies. Suitable control compounds will be selected depending upon the reporter antibodies used in the assay. In general, control compounds should non-specifically bind excess reporter antibodies to function as a positive control to validate the test results. Exemplary control compounds for use with mammalian immunoglobulin-based reporter antibodies include native or recombinant antibody binding proteins such as Protein A, Protein G, Protein A/G, and Protein L, and the like. Other control compounds include anti-species antibodies (e.g., anti-mouse IgG), and the like.

In one or more embodiments, the detection region can comprise multiple defined areas of immobilized antigen. For example, the detection region can comprise a second immobilized antigen (different from the first antigen) and soluble dye in a third defined area of the detection region that is distinct from the first and second defined areas. Fourth, fifth, sixth, etc. defined regions can also be included in the detection region with respective immobilized antigen and soluble dye. In such embodiments, the test article can be used to assay for more than one type of antibody and/or assess the minimum protective antibody levels for more than one type of pathogen. Such multi-plexing assays can be used to determine the necessity of revaccination for several types of pathogens, based upon a single test sample from the patient.

In one or more embodiments, the test article further comprises a second elongated solid support that intersects the first solid support at the detection region. The second solid support comprising a top surface that is co-planar with the first solid support top surface. The second solid support top surface comprises a reporter application region that is in capillary flow communication with said detection region whereby material absorbed on the second solid support may flow by capillary action from the reporter application region to the detection region. Accordingly, there is a region on the top surface of the second solid support between the reporter application region and the detection region that defines a second path of flow of the material. The second solid support will generally have similar characteristics to the first solid support described above. The second elongated solid support can be a test strip or ribbon (with two terminal ends) or other suitable geometric shape to facilitate flow of the material from the reporter application region to the detection region. Any sorbent material (or combination of sorbent materials) can be used for the solid support, as long as it is capable of absorbing, either by capillary action or otherwise, molecules that pass through/along the solid support. The top surface of the solid support will typically be substantially planar or flat, so as not to impede the flow of the reporter fluid, and a porous membrane matrix with a suitable thickness that allows flow through of the reporter fluid. Cellulose-based materials are particularly suited for use as test strips. In one or more embodiments, the second elongated solid support comprises a nitrocellulose membrane covered by an absorbent pad (reporter application region) at or near one end, with the other end intersecting the detection region of the first solid support. Thus, the reporter fluid, after being applied to the reporter application region, wicks up the nitrocellulose membrane, causing the fluid to pass over the detection region as it is "pulled' towards the wicking pad (of the first solid support). Other suitable material for the membrane include nylon, paper, polymers (e.g., polyester, polystyrene, polyacrylamide), activated forms thereof, and the like.

In some embodiments, the reporter application region comprises dried reporter antibodies removably affixed thereto. In this way, activation of the assay during this portion of the testing can be achieved simply by depositing buffer fluid onto the reporter application region to initiate flow of the reporter antibodies along the second path of flow towards the detection region. The reporter antibodies are configured to selectively bind the immobilized antigen and non-selectively bind the control compound in the detection region. Preferably, the reporter antibodies are selected so that they will compete with neutralizing antibodies for binding the designated antigen. In other words, the reporter antibodies will have neutralizing activity and bind neutralizing epitope sites in competition with potential neutralizing antibodies that may be present in the animal test sample.

In one or more embodiments, the solid supports (first and/or second) can be backed by a fluid impervious layer adjacent the porous sorbent top surface layer. The test article can further comprise a cassette or housing for retaining the solid supports. The housing can be formed of any suitable material (e.g., plastic) and any suitable shape that corresponds to the shape of the solid supports. In general, the housing comprises an opening above the sample application region configured to provide access to the sample application pad through the opening (i.e., so that the sample can be deposited onto the sample application region through the opening). Likewise, the housing further comprises an opening above the detection region configured for viewing changes in said detection region. The opening above the detection region can be a true "open" through-hole, or may simply be a clear viewing window. It will also be appreciated that one or more openings may be provided over the detection region. That is, there may be an opening or window for each antigen defined area, or for all antigen defined areas collectively. There may also be a separate opening or window for the control defined area. When present, the housing will further comprise an opening positioned above the reporter application region of the second solid support configured to provide access to the reporter application region (i.e., so that reporter and/or buffer can be deposited onto the reporter application region through the opening).

Methods of the invention can be used to determine the necessity of re-vaccination of an animal against a pathogen, or to measure or quantitate the minimum immunoprotective level of antibodies present in a patient sample against a designated pathogen. Suitable samples for use in the assays include any biological liquid that potentially contains the antibodies of interest, such as blood, serum, and/or plasma from the animal. In one or more embodiments, the methods comprise collecting the biological sample from the animal immediately prior to conducting the assay. That is, an advantage of the inventive platforms is that they can be used in point-of-care testing and analysis of a collected sample in the doctor or veterinarian's office and do not require the sample to be sent away to a laboratory for specialized testing or analysis. In one or more embodiments, the patient sample is first mixed with buffer to dilute it and facilitate capillary flow of the sample through the test device. Exemplary buffers include buffered saline (e.g., PBS). Buffer solutions may include salts, proteins, preservatives, and the like, as long as they do not interfere with antibody binding.

The test sample (including buffer as applicable) is contacted with the test article, and more specifically is deposited or contacted with the sample application region of the first solid support. The test sample flows along the first path of flow passing over the detection region. In doing so, the test sample fluid washes away the soluble dye deposited in the first defined region of the detection region. In the method, the detection region is then observed for the disappearance of the soluble dye from that first defined area of the detection region, as this indicates that the test sample fluid has pass through the detection region (and over the immobilized antigen).

Once the soluble dye is detected as having disappeared, reporter antibodies are then allowed to pass over the detection region. The reporter antibodies are configured so that they will selectively bind to the immobilized antigen, and also non-specifically bind to the control compound. Exemplary reporter antibodies include those having antigen binding domains that compete with neutralizing antibodies (in the patient sample) for binding of neutralizing epitopes, such as glycoprotein of rabies virus. Thus, an advantage of the present assays is that they will be able to differentiate between mere binding and neutralizing antibody titers, because the reporter antibodies will be selected to have neutralizing activity. The reporter antibodies are labelled to generate a detectable signal. In general, this detectable signal may be a color visible in the visual spectrum, but may also be other detectable signals, such as fluorescent signals, electronically-detectable signals, or signals detectable with special optical equipment. Exemplary labels that may be conjugated (covalently or non-covalently) to the reporter antibodies include gold nanoparticles, horseradish peroxidase, and the like. Various labelling techniques are known in the art, it being appreciated that the particular labelling technique must leave the antigen binding domains of the selected reporter antibody available for binding to the antigen target and control.

As the reporter antibody fluid passes over the detection region, it may bind to any open antigens, and preferably neutralizing antigen sites or epitopes, with any excess reporter antibody binding to the control compound. Thus, the first and second defined areas are preferably positioned on the elongated support such that the fluid reaches the second defined (control) area only after passing over the first defined area. Likewise, if there are any other antigen defined areas, the fluid passes over those areas before reaching the second defined area. In other words, the fluid generally reaches the first defined area "first," and in any case preferably reaches the second defined (control) area "last." This applies to the test sample fluid as well.

The detection region is then observed for changes. In the event of a valid test result, the changes will comprise at a minimum, appearance of a detectable signal in the second defined area as a positive control. Accordingly, sufficient fluid (e.g., buffer) should accompany the reporter antibodies to facilitate flow of the antibodies across the entirety of the detection region, such that it crosses the control area, such that a detectable signal should always appear at the second defined region for a valid test. Additional changes that may be detected/observed in the detection region include the appearance of a detectable signal in the first defined area, where the reporter antibodies have bound the immobilized antigen. Appearance of a detectable signal in the first defined region indicates that said animal does not have the minimum immunoprotective level of antibody to said pathogen such that there is a need for re-vaccination of the animal. In other words, even if faintly detectable, the appearance of any detectable signal indicates that the immobilized antigen had "open" positions for binding with the antigen binding domains of the reporter antibodies, even after contact with the patient test sample. Thus, the antibody titers of the animal are below the minimum immunoprotective level of antibodies to the pathogen. Similarly, where the antibody titers of the animal are above the minimum immunoprotective level of antibodies to the pathogen, the immobilized antigen should be completely bound by the anti-pathogen antibodies in the test sample, without any appreciable open" positions for binding with the antigen binding domains of the reporter antibodies. Accordingly, the reporter antibodies will pass over the first defined area, and bind only with the control compound in the second defined area. Thus, there will be an absence of any detectable signal in the first defined area. This indicates that the test animal has antibody above its presumptive minimally-protective level and revaccination of the animal is unnecessary and possibly harmful. The detectable signal will depend upon the particular label selected for the reporter antibodies. In one or more embodiments, the detectable signal is a color viewable in the visible spectrum. In one or more embodiments, the detectable signal appears as a visually discernable line or dot in the first or second defined areas, as applicable.

Various techniques can be used to initiate contact of the detection region with the reporter antibodies. In some embodiments, the test article includes the second elongated solid support that intersects with the detection region of the first solid support. The reporter antibodies can be deposited onto the second solid support where they flow along the second path of flow passing over the detection region. In doing so, the reporter antibodies are brought into contact with the immobilized antigen and the control compound. As noted above, in some embodiments, the second solid support can comprise dried reporter antibodies already deposited onto the reporter application region. Thus, flow of the reporter antibodies can be initiated by deposing sufficient buffer solution onto the reporter application region, which then releases the reporter antibodies so that they can flow by capillary action to the detection region along the second path of flow. In other embodiments, the reporter antibodies can be mixed with sufficient buffer solution, and then this mixture can be deposited onto the reporter application region. The reporter antibodies then flow by capillary action to the detection region along the second path of flow.

The invention also includes kits for use in conjunction with the methods and test article described herein. In one embodiment, the kits effect detection and/or quantitation of minimum anti-rabies antibody levels. The kits comprise the test article as described herein, along with instructions. The instructions may be for using the components of the kit, for practicing the methods of the invention, or both. For example, the instructions may be for collecting a test sample from the animal and testing the test sample using the test article to determine if the animal has a minimum immunoprotective level of antibody against said pathogen such that there is no necessity for re-vaccination of the animal. Reagents or buffers can also optionally be included with the kit.

It will be appreciated by one skilled in the art, that the amount of antigen that will bind (absorb) the indicated amount of antibody listed above as the recommended titer level will vary for each antigen to be tested, as will the amount of detector antibodies. These amounts can be optimized to minimize the reagents needed for each device. The Diagnostic Laboratory at Kansas State University is uniquely positioned to be able to perform the gold-standard assays for immunity against all core canine and feline vaccines. Validation of the proposed testing platform will be completed using this technology and expertise.

The above test, or other similar rapid tests, can be utilized to rapidly detect adequate titer levels for one or more diseases, including those of bacterial origin. The test is preferably run with the solid support sitting on a horizontal flat surface, such that the first and second paths of flow are parallel to the horizontal surface (such as in lateral flow test devices). The unique aspect of this device is that it is being used as a semi-quantitative diagnostic test to indicate ongoing immune protection, rather than being used to detect disease infection. The test can be applied to any animal, including humans, in order to determine the need for vaccination. The test also provides for point-of-care assaying of animal biological samples (as compared to end-of-day or off-site laboratory testing). Thus, the assays can be run immediately after collecting the biological sample from the animal. In addition, each step of the methodology can be completed in mere minutes. For example, the final determination of antibody titer levels can be completed in less than about 20 minutes after collecting the biological sample and applying it to the test article. More particularly, once the sample is applied to the sample application region, the soluble dye in the first defined region will generally be observed to disappear in less than about 5 minutes (preferably less than about 3 minutes). Likewise, once the soluble dye has disappeared from the first defined area, the method can proceed immediately to the next stage, wherein the reporter antibodies are passed over the detection region. The appearance of the control signal will generally be detectable in less than about 5 minutes after applying the reporter antibodies (and preferably less than about 3 minutes). There is no need for application of additional reagents, or chemicals between these steps.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

Spatially relative terms, such as "above," "upper," "beneath," "below," "lower," and the like, may be used herein for ease of description to describe the relationship of one element to another element. It will be understood that the spatially relative terms are intended to encompass different orientations of the apparatus in use or operation in addition to the orientation described. For example, if the apparatus is turned over, elements described as "below" or "beneath" other elements or features would then be oriented "above" the other elements or features. Thus, the exemplary term, "above," may encompass both an orientation of above and below. The apparatus may be otherwise oriented (e.g., rotated 90 degrees or at other orientations) and the spatially relative descriptors used herein interpreted accordingly.

EXAMPLES

The following examples set forth methods in accordance with the invention. It is to be understood, however, that these examples are provided by way of illustration and nothing therein should be taken as a limitation upon the overall scope of the invention.

Example 1

Comparison of Anamnestic Antibody Responses of Dogs and Cats with Current Versus Out-of-Date Vaccination Status Introduction Each year in the United States, approximately 6,000 cases of rabies are documented in animals, primarily in the major wildlife reservoir species (i.e., raccoons, bats, skunks, and foxes). These confirmed cases are invariably associated with 1 or more human or animal exposures to rabies. In addition, many domestic animals come into contact with sick wildlife or other animals that cannot be captured for rabies diagnostic testing and, depending on the geographic location and species of animal involved, may be considered potentially exposed to rabies. As a result, thousands of dogs and cats are known to be exposed or are potentially exposed to rabies each year in the United States.

Regulations have been developed to minimize the public health risks that dogs and cats exposed or potentially exposed to rabies and potentially incubating the virus may pose. These regulations vary, depending on locality, but most public health officials refer to or rely on the Compendium of Animal Rabies Prevention and Control for guidance in these situations.

According to the current version of the compendium, dogs and cats with current rabies vaccination status that have been exposed to an animal confirmed or suspected to be rabid should immediately receive a rabies booster vaccination and be observed for 45 days, most often, as allowed by jurisdictional authorities, under the owner's supervision with no contact restrictions. The recommendation for dogs and cats that have never been vaccinated against rabies and that have been exposed to a rabid animal is euthanasia or quarantine for 6 months in a specialized facility.

In contrast, the compendium guidelines are less clear when it comes to recommendations for dogs and cats overdue for a booster vaccination (i.e., dogs and cats with out-of-date rabies vaccination status), suggesting that these animals be evaluated on a case-by-case basis that takes into account the severity of the exposure, time since the last rabies vaccination, number of rabies vaccinations received previously, current health status of the animal, and local rabies epidemiology. Unfortunately, this recommendation for a case-by-case risk assessment coupled with concerns for public safety, a fear of liability, and the lack of published clinical data regarding response to rabies vaccination in dogs and cats with an out-of-date rabies vaccination status commonly leads to conservative handling of these animals. Most often, this means that public health officials consider these animals to be unvaccinated, resulting in either euthanasia or a 6-month quarantine.

The present study was designed to provide greater insight into the appropriate handling of dogs and cats with out-of-date rabies vaccination status that have been exposed to rabid animals. Specifically, the purpose of the study reported here was to compare anamnestic antibody responses of dogs and cats with current versus out-of-date rabies vaccination status.

Serum samples were obtained from 74 dogs and 33 cats that had been exposed to rabies and brought to a veterinarian for proactive serologic monitoring or that had been brought to a veterinarian for booster rabies vaccination. Blood samples were collected on the day of initial evaluation (day 0) and then again five to fifteen days later. On day 0, a rabies vaccine was administered according to label recommendations. Paired serum samples were analyzed for antirabies antibodies by means of a rapid fluorescent focus inhibition test. All animals had an antirabies antibody titer ≥0.5 IU/mL five to fifteen days after booster vaccination. Dogs with an out-of-date vaccination status had a higher median increase in titer, higher median fold increase in titer, and higher median titer following booster vaccination, compared with dogs with current vaccination status. Most (26/33) cats, regardless of rabies vaccination status, had a titer ≥12 IU/mL, five to fifteen days after booster vaccination. Results indicate that dogs with out-of-date vaccination status were not inferior in their antibody response following booster rabies vaccination, compared with dogs with current vaccination status. These findings support immediate booster vaccination followed by observation for 45 days of dogs and cats with an out-of-date vaccination status that are exposed to rabies, as is the current practice for dogs and cats with current vaccination status.

Materials and Methods

Sample acquisition—The first phase of the study involved serum samples from 10 dogs and 2 cats, from 8 states, that had been exposed to rabies and for which the attending veterinarian or owner had contacted the Rabies Diagnostic Laboratory at Kansas State University between March 2010 and June 2012 for help in assessing the immune state of the animal. The remainder of the study involved serum samples from an additional 64 dogs and 31 cats that had been exposed to rabies and brought to a veterinarian for proactive serologic monitoring or that had not been exposed to rabies and had been brought to a veterinarian for booster rabies vaccination. In total, serum samples from 74 dogs and 33 cats from 13 states collected over a period of 3.75 years were included. The study protocol was approved by the Kansas State University Institutional Animal Care and Use Committee (protocol No. 3193).

For each animal included in the study, a 2-mL serum sample was obtained at the time of initial evaluation (day 0) and then again 5 to 15 days later. On day 0, a rabies vaccine of the attending veterinarian's choice was administered to the animal according to label recommendations. Serum samples were shipped fresh to the Rabies Diagnostic Laboratory and analyzed for antirabies antibody titer using a rapid fluorescent focus inhibition test.

Classification of rabies vaccination status—All dogs and cats included in the study were classified as having a current or out-of-date rabies vaccination status. Rabies vaccination status was classified as current if the animal had received initial rabies vaccination and the initial (i.e., day 0) serum sample was obtained <1 year after the initial vaccination or if the animal had received both an initial rabies vaccination and a rabies booster vaccination and the initial (day 0) serum sample was obtained <3 years after the last vaccination. Otherwise, rabies vaccination status was classified as out of date.

A cutoff of 3 years since the last vaccination was used regardless of whether the last vaccine administered had been licensed for a 1-year or 3-year duration, because the antigenic mass, carrier, adjuvant, and other characteristics of 1-year and 3-year vaccines from two companies were reportedly identical. One animal that received a 1-year vaccine was excluded from the data analysis because the company that manufactured the vaccine would neither confirm nor deny that its 1-year and 3-year formulations were identical.

Rapid fluorescent focus inhibition test—The rapid fluorescent focus inhibition test, a serum neutralization test, was used to determine the titer of rabies neutralizing antibodies in all serum samples. Briefly, rabies virus was mixed with serial dilutions of each serum sample, and the resulting mixture was incubated at 37° C. for 90 minutes. Baby hamster kidney cells suspended in Eagle minimum essential medium with 10% fetal bovine serum were then added, and the mixture was incubated for 20 to 24 hours at 37° C. Following fixation with 80% acetone, a conjugate of antirabies antibody labeled with fluorescein isothiocyanate was added to the cells. After washing, cells were counted by fluorescent microscopy to determine the ratio of infected to non-infected cells at each dilution. Results were compared with results for a standard control sample containing a known neutralizing antibody concentration to determine the titer for each test sample.

End point dilution was not used to determine the specific antibody titer for samples that resulted in complete neutralization of the virus at the highest serum dilution used. However, the maximum possible titer varied between test runs depending on the control sample's ability to neutralize the challenge virus. Standard operating procedures for the test method defined a priori an acceptable range of titers for the control sample, with testing repeated if the titer for the control sample was outside the acceptable range. Because the lowest titer for control samples used in the present study was 12 IU/mL, for calculation purposes, we reported results for test samples >12 IU/mL as 12 IU/mL. In the statistical analysis, all titers reported as ≥12 IU/mL were treated as right censored. For comparison, a rabies neutralizing antibody titer ≥0.5 IU/mL is considered by the World Health Organization to be an adequate vaccine response for dogs and cats traveling to rabies-free areas.

Data analysis—Rabies neutralizing antibody titers following booster vaccination (i.e., days 5 to 15) were compared between dogs with current versus out-of-date vaccination statuses by modeling the proportions of animals with titers exceeding various given values (sometimes referred to as a reverse cumulative distribution). This approach was selected to account for the right censoring of titers for some animals. A proportional hazards model was used to compare distributions of titers between the 2 groups (current vaccination status versus out-of-date vaccination status), with current vaccination status as the reference. In essence, the proportional hazards ratio represented the comparative ability of the 2 groups to reach a particular titer after booster vaccination on day 0. If the ratio was equal to 1, the 2 groups were considered identical. If the ratio was >1, then the response to booster vaccination in animals with an out-of-date vaccination status was considered to be not as robust as the response in animals with a current vaccination status. Conversely, if the ratio was <1, the response to booster vaccination in animals with an out-of-date vaccination status was considered superior to the response in animals with a current vaccination status. For purposes of the present study, we assumed the response to booster vaccination in animals with an out-of-date vaccination status was not clinically worse than the response in animals with a current vaccination status if the hazard ratio was <1.25. On the basis of an analysis of data from Mansfield et al. (Factors affecting the serological response of dogs and cats to rabies vaccination. Vet Rec 2004; 154: 423-426), this choice of non-inferiority margin was determined to be conservative. Formally, in the hypothesis test of non-inferiority, the null hypothesis was that the ratio was ≥1.25 (i.e., out-of-date vaccination status was inferior to current vaccination status), and the alternative hypothesis was that the ratio was <1.25 (i.e., out-of-date vaccination status was non-inferior to current vaccination status). Diagnostic graphs indicated the proportional hazard model was appropriate for these data.

Results

Rabies neutralizing antibody titers for the 10 dogs and 2 cats in the first phase of the study were summarized (Table 1). For all 12 animals, antibody titers 5 to 15 days after booster vaccination were >0.5 IU/mL. Five of the animals were classified as having a current vaccination status, and 7 were classified as having an out-of-date vaccination status. All 7 animals with an out-of-date vaccination status and 2 animals with a current vaccination status were quarantined for 6 months, during which time no rabies-associated clinical disease was reported. All 12 animals survived following rabies exposure. The 2 animals with current vaccination status that were quarantined had been exposed >1 year (but <3 years) after receiving a rabies vaccine labeled for 1-year duration. However, the manufacturer confirmed that the 1-year and 3-year formulations of this product were identical; therefore, for purposes of the present study, both animals were classified as having a current vaccination status.

TABLE 1

Rabies neutralizing antibody titers immediately prior to (baseline) and 5 to 15 days after booster vaccination in 10 dogs and 2 cats that had been exposed to an animal confirmed or suspected to be rabid.

| Species | Exposure description | >1 vaccine dose previously | Label duration of last vaccine (y) | Time since last vaccination (mo) | Rabies vaccination status | Baseline titer (IU/mL) | Titer after booster vaccination (IU/mL) |
|---|---|---|---|---|---|---|---|
| Dog* | Contact with skunk | Yes | 3 | 39.0 | OOD | 9.7 | 12 |
| Dog | Exposed to rabid skunk | Yes | UK | 9.0 | C | 0 | 12 |
| Dog* | Raccoon bite | Yes | 3 | 41.4 | OOD | 12 | 12 |
| Dog* | Raccoon bite | Yes | 1 | 18.1 | C | 0.7 | 3.4 |
| Dog* | Exposed to rabid skunk | No | 1 | 36.0 | OOD | 0.6 | 12 |
| Dog | Exposed to rabid skunk | Yes | 3 | 15.6 | C | 12 | 12 |
| Dog* | Exposed to rabid skunk | No | 1 | 15.6 | OOD | 0.2 | 12 |
| Dog* | Exposed to rabid skunk | No | 1 | 15.4 | OOD | 0.6 | 12 |
| Dog* | Raccoon bite | Yes | 1 | 30.5 | C | 1.8 | 12 |
| Dog | Exposed to rabid skunk | Yes | 3 | 10.7 | C | 3.1 | 12 |
| Cat* | Raccoon bite | Yes | 3 | 38.7 | OOD | 0.3 | 12 |

TABLE 1-continued

Rabies neutralizing antibody titers immediately prior to (baseline) and 5 to 15 days after booster vaccination in 10 dogs and 2 cats that had been exposed to an animal confirmed or suspected to be rabid.

| Species | Exposure description | >1 vaccine dose previously | Label duration of last vaccine (y) | Time since last vaccination (mo) | Rabies vaccination status | Baseline titer (IU/mL) | Titer after booster vaccination (IU/mL) |
|---|---|---|---|---|---|---|---|
| Cat* | Exposed to bat | Yes | 3 | 44.9 | OOD | 12 | 12 |

*Quarantined for 6 months after rabies exposure; no animals developed signs of rabies-associated disease during quarantine, and all 12 animals survived.
C = Current.
OOD = Out of date.
UK = Unknown.

Rabies vaccination status was classified as current if the animal had received an initial rabies vaccination and the initial serum sample was obtained <1 year after the initial vaccination or if the animal had received both an initial rabies vaccination and a rabies booster vaccination 1 year later and the baseline serum sample was obtained <3 years after the last vaccination. Otherwise, rabies vaccination status was classified as out of date. A cutoff of 3 years since the last vaccination was used regardless of whether the last vaccine administered had been licensed for a 1-year or 3-year duration, because formulations of the 1-year and 3-year vaccines were confirmed by the manufacturer to be identical.

Rabies neutralizing antibody titers before (day 0) and after (day 5 to 15) booster vaccination for all 74 dogs and 33 cats included in the study were summarized, along with median increase in titer and median fold increase (Table 2). Dogs with out-of-date vaccination status had a higher median increase in titer, higher median fold increase in titer, and higher median titer following booster vaccination, compared with dogs with current vaccination status. However, statistical analyses were not performed on these parameters.

TABLE 2

Rabies neutralizing antibody titers immediately before (baseline) and 5 to 15 days after booster vaccination in 74 dogs and 33 cats classified as having a current or out-of-date rabies vaccination status.

| Species and vaccination status | Baseline titer (IU/mL)* | Titer after booster vaccination (IU/mL)* | Median increase (IU/mL) | Median fold rise |
|---|---|---|---|---|
| Dog | | | | |
| Current (n = 55) | 2.6 (0-12) | 11.1 (0.5-12) | 3.1 | 0 |
| Out of date (n = 19) | 2.0 (0-12) | 12.0 (0.5-12) | 8.1 | 2 |
| Cat | | | | |
| Current (n = 7) | 2.4 (0.1-12) | 12.0 (2.6-12) | 9.4 | 2 |
| Out of date (n = 26) | 6.3 (0.3-12) | 12.0 (2.9-12) | 2.4 | 0 |

*Data are given as median (range).
See Table 1 for remainder of key.

The percentages of dogs and cats in each vaccine category with titers that equaled or exceeded various benchmarks above 0.5 IU/mL were summarized (Table 3). All animals in the study had a titer ≥0.5 IU/mL 5 to 15 days after booster vaccination. This included the 14 dogs (9 with current vaccination status and 5 with out-of-date vaccination status) and 2 cats (1 with current vaccination status and 1 with out-of-date vaccination status) that had titers <0.5 IU/mL prior to booster vaccination (day 0; Table 4). Median increase in titer for dogs (Table 5) and cats (Table 6) with an out-of-date vaccination status was higher for those that had previously received only a single dose of vaccine, compared with those that had previously received ≥2 doses of vaccine. Again, however, no statistical analyses were performed on this parameter.

TABLE 3

Number (percentage) of dogs and cats in Table 2 with rabies neutralizing antibody titers 5 to 15 days after booster vaccination that equaled or exceeded various benchmarks above 0.5 IU/mL.

| Species and vaccination status | Titer (IU/mL) | | | | | |
| | 0.5 | 1.0 | 2.0 | 4.0 | 8.0 | 12.0 |
|---|---|---|---|---|---|---|
| Dog | | | | | | |
| Current (n = 55) | 55 (100) | 53 (96) | 50 (90) | 40 (72) | 34 (61) | 26 (47) |
| Out of date (n = 19) | 19 (100) | 18 (94) | 18 (94) | 16 (84) | 13 (68) | 13 (68) |

TABLE 3-continued

Number (percentage) of dogs and cats in Table 2 with rabies neutralizing antibody titers 5 to 15 days after booster vaccination that equaled or exceeded various benchmarks above 0.5 IU/mL.

| Species and vaccination status | Titer (IU/mL) | | | | | |
|---|---|---|---|---|---|---|
|  | 0.5 | 1.0 | 2.0 | 4.0 | 8.0 | 12.0 |
| Cat | | | | | | |
| Current (n = 7) | 7 (100) | 7 (100) | 7 (100) | 6 (85) | 6 (85) | 6 (85) |
| Out of date (n = 26) | 26 (100) | 26 (100) | 26 (100) | 23 (88) | 23 (88) | 21 (80) |

Data are given as number (%).
See Table 1 for remainder of key.

TABLE 4

Rabies neutralizing antibody titers immediately before (baseline) and 5 to 8 days after booster vaccination in 14 dogs and 2 cats with a titer <0.5 IU/mL prior to booster vaccination.

| Species and vaccination status | Baseline titer (IU/mL) | Time between samples (d) | Titer after booster vaccination (IU/mL) |
|---|---|---|---|
| Dog | | | |
| Out of date | 0.2 | 8 | 12 |
|  | 0.2 | 7 | 12 |
|  | 0 | 5 | 12 |
|  | 0.4 | 7 | 2.4 |
|  | 0 | 8 | 0.5 |
| Current | 0 | 7 | 12 |
|  | 0.4 | 7 | 4.4 |
|  | 0.3 | 5 | 11.1 |
|  | 0.4 | 7 | 0.5 |
|  | 0.1 | 7 | 1.3 |
|  | 0.1 | 7 | 6.1 |
|  | 0 | 7 | 2 |
|  | 0.1 | 5 | 4 |
|  | 0.3 | 6 | 0.5 |
| Cat | | | |
| Out of date | 0.3 | 5 | 12 |
| Current | 0.1 | 6 | 12 |

Median titer after booster vaccination was 12 IU/mL for dogs with an out-of-date vaccination status and 4 IU/mL for dogs with a current vaccination status.
See Table 2 for key.

TABLE 5

Rabies neutralizing antibody titers immediately before (baseline) and 5 to 15 days after booster vaccination for 15 dogs with an out-of-date vaccination status classified on the basis of number of rabies vaccinations received previously.

| No. of vaccine doses received previously | Baseline titer (IU/mL) | Time between samples (d) | Titer after booster vaccination (IU/mL) | Time overdue for vaccination (mo) | Increase in titer (IU/mL) |
|---|---|---|---|---|---|
| ≥2 | 0.6 | 6 | 2.8 | 0.2 | 2.2 |
|  | 0.4 | 7 | 2.4 | 0.3 | 2 |
|  | 9.7 | 15 | 12 | 3 | 2.3 |
|  | 4 | 7 | 5.9 | 4.8 | 1.9 |
|  | 12 | 6 | 12 | 7.5 | 0 |
|  | 3.9 | 7 | 12 | 10.6 | 8.1 |
|  | 2.9 | 7 | 7.8 | 14.9 | 4.9 |
|  | 0 | 8 | 0.5 | 19.7 | 0.5 |
|  | 2 | 7 | 12 | 22.8 | 10 |
| 1 | 3.4 | 7 | 12 | 0.3 | 8.6 |
|  | 0.6 | 10 | 12 | 3.4 | 11.4 |
|  | 0.2 | 8 | 12 | 3.6 | 11.8 |
|  | 0 | 5 | 12 | 5.9 | 12 |
|  | 0.6 | 7 | 12 | 24 | 11.4 |
|  | 0.2 | 7 | 12 | 36.1 | 11.8 |

Median increase in titer was 2.2 IU/mL for dogs that had previously received ≥2 doses of vaccine and was 11.6 IU/mL for dogs that had previously received only a single dose of vaccine.

TABLE 6

Rabies neutralizing antibody titers immediately before (baseline) and 5 to 15 days after booster vaccination for 24 cats with an out-of-date vaccination status classified on the basis of number of rabies vaccinations received previously.

| No. of vaccine doses received previously | Baseline titer (IU/mL) | Time between samples (d) | Titer after booster vaccination (IU/mL) | Time overdue for vaccination (mo) | Increase in titer (IU/mL) |
|---|---|---|---|---|---|
| ≥2 | 12 | 8 | 12 | 0.1 | 0 |
|  | 6.1 | 7 | 11.3 | 0.1 | 5.2 |
|  | 12 | 8 | 12 | 0.1 | 0 |
|  | 3.4 | 7 | 12 | 0.2 | 8.6 |
|  | 12 | 7 | 12 | 0.2 | 0 |
|  | 5.4 | 6 | 12 | 0.9 | 6.6 |
|  | 6.4 | 7 | 9 | 1.1 | 2.6 |
|  | 12 | 7 | 12 | 2.3 | 0 |
|  | 12 | 7 | 12 | 2.5 | 0 |
|  | 0.3 | 5 | 12 | 2.7 | 11.7 |
|  | 3.4 | 7 | 3.7 | 2.9 | 0.3 |
|  | 12 | 7 | 12 | 2.9 | 0 |
|  | 8.9 | 7 | 12 | 3.2 | 3.1 |
|  | 12 | 7 | 12 | 3.7 | 0 |
|  | 12 | 7 | 12 | 5.6 | 0 |
|  | 2.5 | 7 | 12 | 5.6 | 9.5 |
|  | 2.4 | 7 | 12 | 8.4 | 9.6 |
|  | 12 | 8 | 12 | 8.9 | 0 |
|  | 2.4 | 6 | 12 | 15.9 | 9.6 |
|  | 3 | 6 | 3.3 | 34.6 | 0.3 |
|  | 0.6 | 7 | 2.9 | 46.1 | 2.3 |
| 1 | 0.6 | 5 | 12 | 4.9 | 11.4 |
|  | 9.6 | 6 | 12 | 21.2 | 2.4 |
|  | 2.7 | 6 | 12 | 38.5 | 9.3 |

Median increase in titer was 0.3 IU/mL for cats that had previously received ≥2 doses of vaccine and was 9.3 IU/mL for cats that had previously received only a single dose of vaccine.

Figure 1:
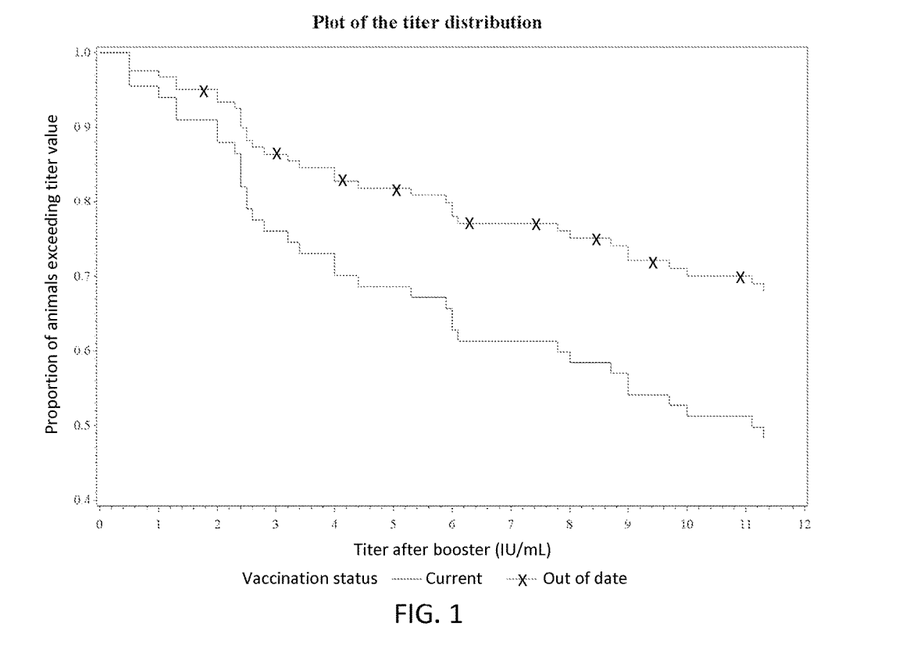

Reverse cumulative distributions of titers 5 to 15 days after booster vaccination were calculated for dogs with current vaccination status and dogs with out-of-date vaccination status (FIG. 1). The hypothesis test for noninferiority was significant (P=0.029), with out-of-date dogs shown to be non-inferior to current dogs, and the proportional hazards ratio (with current vaccination status as the reference) was 0.53 (95% confidence interval, 0.20 to 1.12). Because the upper limit of the 95% confidence interval was <1.25, the response to booster vaccination in dogs with an out-of-date vaccination status was considered to be non-inferior to the response in dogs with a current vaccination status.

Because of the small number of cats in the study and the fact that most cats, regardless of whether they had a current (6/7) or out-of-date (21/26) vaccination status, had a titer ≥12 IU/mL 5 to 15 days after booster vaccination, proportional hazards analysis could not be used to analyze the response to booster vaccination in cats with current versus out-of-date vaccination status.

Discussion

Results of the present study indicated that the anamnestic responses of dogs and cats with an out-of-date rabies vaccination status were similar to the responses in animals with a current rabies vaccination status. Specifically, titers 5 to 15 days after booster vaccination in dogs with an out-of-date vaccination status were shown to be non-inferior to titers in dogs with a current vaccination status. Also, dogs with an out-of-date vaccination status had a higher median increase in titer, higher median fold increase in titer, and higher median titer following booster vaccination, compared with dogs with current vaccination status; however, statistical analyses were not performed to compare these parameters between groups.

The non-inferiority margin of 1.25 used in the present study was selected because it has commonly been used in other studies as a conservative margin for hazard ratio analyses. On the basis of an analysis of results reported by Mansfield et al. for dogs and cats vaccinated with 3 rabies vaccines, we determined that a margin of 1.25 corresponded to a difference in titer between animals with an out-of-date vaccination status and naïve animals that was at least 88% of the difference in titer between animals with current vaccination status and naïve animals. Ng recommends that the non-inferiority margin preserve at least 80% of the advantage the active treatment holds over placebo. (Ng, Non-inferiority hypotheses and choice of non-inferiority margin. Stat Med 2008; 27: 5392-5406.) Therefore, we believe that the non-inferiority margin of 1.25 used in the present study was conservative.

In the present study, we used 3 methods to compare anamnestic responses to rabies vaccination in dogs and cats with current versus out-of-date vaccination status: fold rise in titer, absolute increase in titer, and absolute titer following booster vaccination. Evaluating the fold rise in titer gives an advantage to animals with a low starting titer. Therefore, because many animals in the present study with an out-of-date vaccination status had lower starting titers, we were not surprised that they had a higher fold rise in titer, compared with animals with a current vaccination status.

Although absolute increase in titer following booster vaccination provides some information on the anamnestic response to vaccination, it may not represent a true measure of protection. Assuming that neutralizing antibody titer is a measure of protection, then a rabies neutralizing antibody titer of 5.5 IU/mL should afford better protection than a titer of 0.5 IU/mL. However, when evaluating absolute increase in titer, an increase from 0.1 to 0.5 IU/mL is the same as an increase from 5.1 to 5.5 IU/mL.

In contrast to fold-rise or absolute increase in titer, absolute titer following booster vaccination should provide a good indication of the level of protection achieved. In the present study, we found that the response for dogs with an out-of-date vaccination status was non-inferior to the response for dogs with a current vaccination status (P=0.029). Unfortunately, we could not perform the same analyses for cats in the present study because of the low number of cats enrolled and the fact that most cats, regardless of whether they had a current or out-of-date vaccination status, achieved the maximum titer (≥12 IU/mL) after booster vaccination. Given these high titers, even if a difference had been found between groups, it likely would not have been clinically meaningful.

Results of the present study may help clarify recommendations in the Compendium of Animal Rabies Prevention and Control for post-exposure management of dogs and cats overdue for a booster vaccination that are exposed to an animal confirmed or suspected to be rabid. Currently, the guidelines recommend that such animals be evaluated on a case-by-case basis on the basis of the following 5 criteria: severity of the exposure, time since the last rabies vaccination, number of rabies vaccinations received previously, current health status of the animal, and local rabies epidemiology.

Importantly, the guidelines do not recommend altering post-exposure management for dogs and cats with a current vaccination status on the basis of severity of the exposure. Considering that dogs and cats in the present study responded to rabies booster vaccination in a similar manner regardless of whether they had a current or out-of-date vaccination status, we believe that post-exposure management should be the same for dogs and cats with current versus out-of-date vaccination status, regardless of the severity of exposure.

With respect to time since the last rabies vaccination, we did not identify a difference in anamnestic response between animals with current versus out-of-date vaccination status. In fact, dogs with an out-of-date vaccination status generally had higher responses than did dogs with a current vaccination status.

Similarly, with respect to the number of rabies vaccinations received previously, we did not find a substantial difference in anamnestic responses between dogs and cats that had previously received only a single dose of vaccine and those that had received ≥2 doses previously. However, age could have been a confounding factor, given that animals vaccinated only once had a median age of 3 years, whereas animals vaccinated multiple times had a median age of 6 years, and immunosenescence in dogs and cats is well documented.

We did not evaluate the effect of health status on anamnestic responses in the present study, and all animals were generally healthy. However, we recommend that, regardless of vaccination status, public health officers should be cautious when managing immunocompromised dogs and cats that have been exposed to rabid animals.

Finally, in suggesting that public health officials take local rabies epidemiology into consideration in the post-exposure management of dogs and cats with an out-of-date vaccination status that have been exposed to an animal suspected to be rabid, the compendium acknowledges that although rabies is endemic in the United States, the incidence varies widely from one location to the next. Thus, without confirmatory testing, the risk that a dog bitten by a wild raccoon has truly been exposed to rabies is much lower in, for example, Illinois than in Alabama. Nevertheless, given that the response to rabies booster vaccination in the present study was similar regardless of rabies vaccination status, we believe that post-exposure management should be the same.

In conclusion, results of the present study indicated that the anamnestic response to rabies booster vaccination in dogs and cats with an out-of-date vaccination status is similar to the response for dogs and cat with a current vaccination status. Thus, we believe that post-exposure management of any previously vaccinated dog or cat exposed to a confirmed or suspected rabid animal should be the same, regardless of vaccination status. Specifically, we believe that appropriate post-exposure management for dogs and cats with an out-of-date vaccination status is immediate booster vaccination followed by observation for 45 days, rather than euthanasia or quarantine for 6 months. If additional reassurance is needed, titers could be measured prior to and again 5 to 7 days after booster vaccination to determine whether an anamnestic response has occurred.

Example 2

Confirmation of Antibody Titers as a Measure of Necessity of Vaccination

Introduction

The elimination of dog to dog transmitted rabies virus in North America is perhaps one of the greatest accomplishments in zoonotic disease control in the United States. In 1946, the same year the Public Health Service initiated a national rabies control program, over 8,000 dogs were confirmed as rabid, resulting in 33 human deaths. Minimizing this disease in humans was due to controlling the disease in dogs; municipal licensing of owned dogs and of elimination of stray/unwanted animals played no small part in these efforts. However, the most important step in elimination this scourge was the advent of efficacious and liberal use of, vaccination in dogs against the rabies virus. Vaccination of pets keeps the incidence of this disease in dogs and cats to a minimum and has eliminated them as a reservoir for the virus. Vaccination against rabies in domestic animals is still the most important step to avoid human contact with this disease in the United States.

For all the benefits afforded by vaccination against rabies virus, there are recognized risks in multiple vaccinations, for both rabies and many other diseases of domestic animals. As veterinary care improves, domestic pets are living longer lives. This increases the need for further vaccination as well as the probability of vaccination side-effects. As society evolves and pets become more important in peoples' lives, these side-effects are becoming less tolerated. Currently, the American Veterinary Medical Association (AVMA), the American Animal Hospital Association (AAHA) and the American Association of Feline Practitioners (AAFP) all have adopted standards allowing use of serologic assays to determine the necessity of booster vaccination for all core vaccinations, except rabies.

The reason cited by these organizations for the lack of serologic antibody titer standards against rabies is state and local laws mandating routine (every 1 or 3 years) vaccination. Most municipalities in the United States require licensing of dogs, and to a lesser extent cats, which is dependent upon a current vaccination certificate. The current standard that many states utilize for guidance for their regulations is the Compendium of Animal Rabies Prevention and Control (Compendium) published by the National Association of State Public Health Veterinarians (NASPHV). The current edition states:

RABIES SEROLOGY: Some jurisdictions require evidence of vaccination and rabies virus antibodies for animal importation purposes. Rabies virus antibody titers are indicative of a response to vaccine or infection. Titers do not directly correlate with protection because other immunologic factors also play a role in preventing rabies, and our abilities to measure and interpret those other factors are not well-developed. Therefore, evidence of circulating rabies virus antibodies in animals should not be used as a substitute for current vaccination in managing rabies exposures or determining the need for booster vaccinations.

However, a careful review of existing data shows that antibody titers against rabies virus do correlate to survival. Evidence of this will be presented along with a framework whereby serologic titers can be utilized to recommend vaccination against rabies as needed and upon an individual basis.

Consequences of Vaccination—Historically the veterinary profession has considered vaccination a relatively innocuous medical procedure as evidenced by the fact that in most states, most vaccines can still be purchased over the counter. The standard operating procedures in veterinary practices has been "when in doubt, vaccinate the patient" believing the benefits of vaccinations always outweigh any possible risks. However the emerging awareness of acute and chronic adverse reactions to vaccines is changing the way vaccine decisions are being made in small animal practices. The current trend is to carefully assess each patient's disease risk to determine if vaccine(s) are necessary and if so, which vaccine(s) would be appropriate. The use of serological titers can be a valuable tool in making those vaccine decisions. The concern for proper use of vaccinations is examined in two guiding publications. The AAHA published the 2011 Canine Vaccine Guidelines and the AAFP has posted 2013 Feline Vaccination Advisory Panel Report. Each is the most recent edition of an on-going series of reports. The common theme through both is that vaccines have been important in controlling the spread of infectious diseases of the dog and cat and that generally any risks associated with vaccination is far out-weighed by the risk each agent poses if an animal is not vaccinated. Despite the low risk, vaccination introduces foreign and highly antigenic material so can in some instances cause moderate to severe unintended consequences. The AAHA lists reactions such as, injection-site reactions, allergic or immune-mediated reactions, tumorogenesis and vaccine-induced immunosuppression as possible adverse events due to vaccination. The AAFP similarly lists anaphylaxis and allergic reactions, along with injection-site sarcomas (FISS) as the major reported adverse reactions to vaccination of cats. While both documents recognize that adverse reactions are under-reported; AAHA does not report a rate of adverse reactions in dogs while AAFP reports a general rate of reactions as 51.6/10,000 cats vaccinated. Anaphylaxis is reported as 1-5 cases per 10,000 vaccine dose while FISS are reported as 13-36/10,000 doses.

The growing concern for FISS can be evaluated by the responses throughout veterinary care. The Vaccine-Associated Feline Sarcoma Task Force (VAFSTF) was formed in 1996 and reported their findings in a comprehensive report in March, 2001. Outcomes from this report include suggested follow up on vaccine-site masses as well as the recommendation that rabies and FELV vaccines, those most implicated in FISS be given as distally as possible using either limbs or tail. Recent studies from the United States and Canada, show that the site of feline sarcomas has indeed shifted from the interscapular region to hind limbs. Despite better long-term outcomes for cats affected by FISS, this only proves to enforce the causation of FISS. Industry has responded to the side effects of vaccination and contributed by formulating vaccines utilizing recombinant technology without adjuvants (Purevax, Merial, Athens, Ga.), as well as vaccine that come in a smaller dose for cats (ULTRA Duramune, Boehringer Ingelheim, St. Joseph, Mo.). However, research has shown that the marketing of recombinant-live vaccines without adjuvant, had made no significant change in the occurrence of sacrcomas in cats. Side effects due to vaccinations, whether real or anecdotal, are increasingly less tolerable to the pet owning public. Continually exposure to vaccination also raises the risk of immunosenesence and inflammaging in our older pets.

Vaccine-induced immunity is a multifaceted process involving antigen processing, humoral immunity, cell mediated immunity, local immunity and cell memory. Predicting whether a patient is protected against a disease based solely on a single serum titer is a gross over simplification of this complex immune process. However, despite the drawbacks, the use of serum titers in making logical and informed vaccine-related decisions is gaining some popularity especially in animals with histories of a previous vaccine reaction, or in those individuals prone to allergic reactions, or in those specific cases where concerns of "over vaccinations" persist. Dr. Klinborg of the AVMA Council of Biologic and Therapeutic Agents (COBTA) perhaps captured the entirety of the issue when he wrote.

While the risks to animal health from nonvaccination are significant, vaccine use should be limited to creating only clinically relevant immunity. Not all vaccines are indicated for all animals, and there is variability among products marketed for use against the same disease. Revaccination of an animal already protected does not result in enhanced disease resistance, but may result in increased risk of adverse postvaccination events.

Some animals have trouble mounting an adequate immune to several of the core vaccines and management of these animals could be improved if their immune status was be evaluated by serology rather than assuming they are protected because of recent vaccination. The obvious intersection of these issues is serological assessment and application of booster doses of vaccine on an individual, and only as needed basis.

Immune response to rabies virus infection and vaccination—Rabies virus is passed to a new animal host through the bite from an infected animal. The incubation period in animals is both long and highly variable. This protracted incubation means that the virus is exposed to a range of host defenses. Yet through this barrage of events the virus maintains and causes one of the mankind's most feared infections with a mortality rate of nearly 100%. In order for this to happen, rabies virus has evolved a range of defenses to thwart the host's immune system.

The first line of defense against any pathogen is the innate immunity. This response is not pathogen specific; the response to a particular pathogen is the adaptive immune system. Innate immunity is a system that results in the release of immune cytokines, including interferons (IFN), and attraction of immune cells in the area of the initial infection. Rabies virus has been shown to evade host innate immune responses through several mechanisms. The phosphoprotein (P) of rabies virus has been shown to down regulate the production of IFN, which induces a virus-resistant state in cells. Rabies virus also cause changes in infected neurons that cause tolerance of infected cells by invading T-cells, as well as inducing apoptosis in T-cells. By the time the adaptive immunity is coming on line, the virus has reached the central nervous system (CNS) which is generally thought to be an immune-privileged site.

Evaluating the host immune response to infection with rabies virus indicates that the adaptive immune system misses the window before the virus is protected within the CNS. The picture of human clinical cases in the United States, the United Kingdom and Thailand is of a very late humoral immune response. In human patients where titers in serum and cerebrospinal fluid (CSF) are performed, most do not develop anti-rabies titers until well into the clinical course of the disease. [32] Several researches have reported naturally induced (non-vaccine) anti-rabies titers in several species including bats and raccoons. The theory is that these animals indicate abortive rabies infections. The antibody response in these animals seems to indicate the importance of a specific antibody response in order to stop an infection.

Studies using attenuated rabies strain CVS-F3 show a transient infection which normal mice are able to survive when inoculated intramuscularly (IM) and which induces production of anti-rabies antibodies in inoculated animals. Normal mice when infected intra-nasally (IN), the disease is more detrimental, with animals showing depression and weight loss but recovery by day 21 post-infection. When mice with induced knock-out of various immune functions (without functional CD8+ T cells, interferons or complement) were infected IN, the clinical course of disease was similar to their normal counterparts. However, when mice without functional B cells or without functional B and T cells were similarly infected, all mice succumbed by day 24. All animals except those without functional B cells developed significant viral neutralizing antibodies (VNA) by day 21. There was evidence of a role for T cells in clearance of virus from the brains of infected animals but the key to survival was development of antibodies.

The antibody response to vaccination in susceptible animals and humans is therefore critical to survival. Neutralizing antibodies are directed at the external glycoprotein (G) and high levels of IgG can be achieved by vaccination with either attenuated, killed whole-virus or protein fraction vaccines. Vaccination along with administration of rabies immune globulins (RIG) is a valuable tool in preventing human disease even after exposure to rabies virus. The patients' immune responses generally peak approximately 30 days following the first vaccination and thus the administration of passive immunity (RIG) is critical to survival. In studies undertaken by the World Health Organization in 1954, people exposed to a rabid wolf in Iran were treated either with vaccine or vaccine in conjunction with RIG. Twelve of 13 patients receiving RIG/vaccination survived while 3 of 5 patients receiving vaccine alone succumbed to infection.

Establishing a Protective Titer in Dogs and Cats

Rabies antibody titers can currently be measured by several methods, the most common being the Rapid Fluorescent Focus Inhibition Test (RFFIT) and the Fluorescent Antibody Viral Neutralization (FAVN). These test show comparable results and replaced the mouse neutralization test (MNT) that was used prior to cell culture assays being developed. All the methods mentioned here are considered serum neutralization (SN) tests and they assure the functionality to kill rabies virus. Rabies titers are currently used to approve vaccines licensed for use in humans, to determine if a human vaccinee is adequately vaccinated or to qualify animals for travel to rabies free countries. However, these same measures are not currently adequate to determine the need for a rabies booster for animals at relatively low risk of exposure in the United States. To establish the international standard for shipping animals to rabies free destinations, an extensive review of the existing literature was undertaken by Aubert (Practical significance of rabies antibodies in cats and dogs. Rev. Sci. Tech. 1992; 11:735-760). He concluded that the standard of 0.5 International Unit per milliliter of serum (IU/mL) should be the cut off to show adequate response to vaccination in dogs and cats. This is the standard that the World Health Organization (WHO) uses for titers in humans to determine the need for booster vaccination. When RIG is given as part of Post Exposure treatment (PEP) in humans, the dosage is given by weight of the patient, when this dose (20 IU/kg) is adjusted to blood-volume it approximates a circulating antibody titer to 0.5 IU/mL.

As demonstrated by Example 1, animals that have lapsed on current vaccination status have an anamnestic response to a rabies booster that is equal to that of currently vaccinated animals. This project was, at its core, an attempt to save the lives of pets with expired vaccinations, based on a date printed on the label. However, pet owners may see this as a policy that allows a 'vaccinate once and forget' mindset. This is not best public health policy, in part because animals cannot self-report exposures and because of the severity and zoonotic nature of the disease. As shown in Example 1, 9 of 55 (16%) of currently vaccinated animals had titers below the 0.5 IU/mL threshold. A similar study from Japan showed that dogs with multiple vaccinations and tested 25 months or more since last vaccination failed to hold titers above 0.5 IU/mL in 16% of animals tested. Other authors have published that animals tested by routine FAVN for transportation to rabies free areas have reported similar numbers of titers below the 0.5 IU/mL threshold of 7.4 and 4.1 percent in dogs and 1.9 and 2.9 percent in cats. These percentages are probably lower than the general animal population since many of these animals have had recent booster doses in preparation for travel. Low responses to vaccination against rabies should come as no surprise because low responders to other core vaccinations of dogs and cats have been identified as well.

One method to assure proper immunity to rabies is to keep antigen content of the vaccinations high. Licensed vaccines used in dogs and cats are subjected to efficacy trials showing survival from lethal challenge in an in vivo model. Utilizing data from these challenges the protective nature of anti-rabies antibodies becomes quite evident. As part of licensing requirements for rabies vaccines, vaccinated animals are challenged with rabies at the end of the testing period. To be qualified by the United States Department of Agriculture Center for Veterinary Biologics (USDA-CVB) for sale, a rabies vaccine must show that the virus challenge was highly virulent by showing that control animals (unvaccinated) are lethally infected at a high rate (80%). At the same time, vaccinated animals must be protected with at least 87% of animals surviving challenge (26 of 30 vaccinates). The Federal regulations concerning potency testing of rabies vaccines (9 CFR 113.209 (2010)) also require that anti-rabies antibodies be measured during the course of the trial including just prior to the inoculation of the animals with the virus. The results of all available challenge studies are presented in Table 7.

TABLE 7

| | titer | | | | |
|---|---|---|---|---|---|
| | <5 | 5-9 | 10-19 | 20-39 | ≥40 |
| | | | dead/challenged | | |
| DOGS | | | | | |
| MSNT | 56/251 | 9/100 | 9/92 | 1/63 | 0/171 |
| RFFIT | 84/241 | 13/112 | 9/119 | 0/87 | 0/201 |
| total | 140/492 | 22/212 | 18/211 | 1/150 | 0/372 |
| CATS | | | | | |
| MSNT | 25/155 | 5/57 | 5/94 | 0/33 | 0/144 |
| RFFIT | 17/87 | 3/59 | 1/62 | 1/49 | 1/187* |
| total | 42/242 | 8/116 | 6/156 | 1/82 | 1/331 |

Table 7 is data from T. O. Bunn (Cat Rabies. In: George M Baer ed. Natural History of Rabies. Boca Raton: CRC Press. 1991: 379-387) and shows dogs and cats categorized into titer ranges for all animals with a positive serology result by either MNT or RFFIT methods which are equivalent measures. Twenty-eight percent of dogs and seventeen percent of cats without detectable antibody levels at the time of challenge succumbed to rabies infection. In dogs, the death loss drops to only 10% with a titer of between 1:5 and 1:9, 8.5% with titers between 1:10 and 1:19, and less than 1% if the rabies titer was above 1:20. No dogs succumbed if the titer was 1:40 or above. The trend is similar in cats with only 7% of cats with titers 1:5 to 1:9 succumbing to challenge, 4% with titers between 1:10 and 1:19 and less than 1% if the titer was above 1:20. There was a single death in a cat that was directly inoculated into the spinal cord that maintained a titer >1:40. However, this animal had neurological symptoms immediately upon injection with the challenge, so is not considered a valid trail and was thrown out of further analyses. Clearly there is a correlation between survival and the antibody titer at the time the challenge in given. Keep in mind that this is made even more impressive when one considers the challenge that the survivors overcome. Typically nearly 100% of the non-vaccinated controls die in the publications cited, and this level of infection rate from natural exposures has never been documented.

Multiple researchers have compiled their survival data measured titers at the time of challenge as either above or below that 0.5 IU/mL threshold. Some researchers have used the standard of 'detectable antibodies' at the time of challenge while others have checked for seroconversion months prior to the virus challenge is applied. This data is hard to compare between studies but generally, 15-20% of dogs and cats with titers below 0.5 IU/mL at challenge, succumb to rabies infection while animals with higher RVNA titers almost always survive. A single cat succumbed during the Kihm trial while maintaining a titer above 0.5 IU/mL. However, the entire study was thrown out because the challenge dose did not meet CVB standards. Of all vaccinated animals, 25% succumbed to challenge showing that the challenge dose was too high and therefore not valid.

The results of these various trials lead Aubert to the conclusions that animals with higher titers have the best chance of surviving challenge and that those with lower or undetectable titers, although most would survive, were the mostly likely to succumb to rabies infection. His final conclusion was that the recognized level of protection in cats was an RVNA titer of 0.1 IU/mL and in dogs an RVNA level of 0.2 IU/mL. This led to the adoption of the 0.5 IU/mL standard as being the level of rabies antibodies required to transport pets into rabies free-areas.

Discussion

One statement that is often referred to, but taken grossly out of context and therefore misinterpreted, is from Keith Sikes. In his 1971 work he notes 'as in many others (studies), presence of rabies SN antibodies at the time of challenge did not indicate protection for all animals.' The confusion created by this single statement has kept animals from benefiting from utilizing titers as measures of protection, while we use the same standard to protect human lives. The misinterpretation lies in the fact that some animals (vaccinated) but with no detectable at the time of challenge, will still survive challenge. However, this is the goal of vaccination. The animals that succumbed to infection in the Sikes trial had titers of only 1:3 and 1:5 at the time of challenge. These titers would equate to a measure of <0.05 IU/mL, which is under or near the lower limit of quantitation (LLOQ) in most rabies serology assays. As shown in the data from Bunn, survival increases with increasing titer, until animals above a certain threshold become virtually uninfectable unless the viral dose is above acceptable ranges. In fact, in 1981 Bunn and Ridpath noted that 'it may not be necessary to challenge all vaccinated dogs in a rabies immunogenicity test, but only those with antibody titers below a given level.' Further they state that 'serology is a valid indicator of rabies immunity. It is hoped that this information will be analysed by those responsible for such regulations (quarantine and vaccination standards) and applied where appropriate.' It is hard to imagine that this data has not been acted on in the 35 years since its publication.

Figure 2:
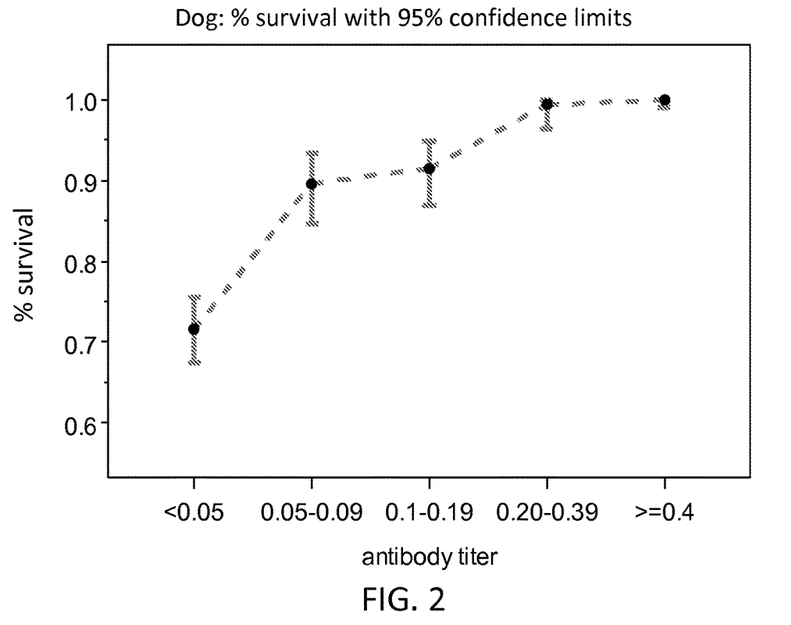
FIG. 2 is a graph analyzing the survival rate of dogs at various antibody titer levels with 95% confidence limits.

When one compares the relative risk of death due to rabies virus infection, assuring that pets maintain a titer above 0.5 IU/mL would be a far more rigorous standard than merely requiring current vaccination status. Given the guidelines for qualification of veterinary biologics, currently vaccinated pets can have 13% animals challenged succumb to infection (an acceptable risk of roughly 1 in 8 animals) and still be considered as an effective vaccine. This risk is validated using the challenge data showing that across all studies, 181 of 1437 (12.6%) vaccinated dogs succumbed to challenge. Cats are actually better protected by vaccination showing that 58 of 927 (6.3%) animals challenge succumbed. Using the Bunn data, a statistical analysis was conducted using Proc FREQ in SAS version 9.3 (SAS Institute, Cary N.C.). The Cochran-Mantel-Haenszel (CMH) test and the Cochran-Armitage (CA) trend test were used to compare the survival rate across the five ordered levels of pre-challenge titer. P-values were all <0.0001. Exact (Clopper-Pearson) 95% confidence limits for the survival rate were computed at each titer level. The results of this analysis for dogs is shown in the Table below, as well as FIG. 2.

TABLE 8

Comparison of Dog Survival Rates.

| titer | % survival | lcl_95 | ucl_95 |
|---|---|---|---|
| <0.05 | 71.5% | 67.3% | 75.5% |
| 0.05-0.09 | 89.6% | 84.7% | 93.4% |
| 0.1-0.19 | 91.5% | 86.9% | 94.9% |
| 0.20-0.39 | 99.3% | 96.3% | 100% |
| >=0.4 | 100% | 99.0% | 100% |

Figure 3:
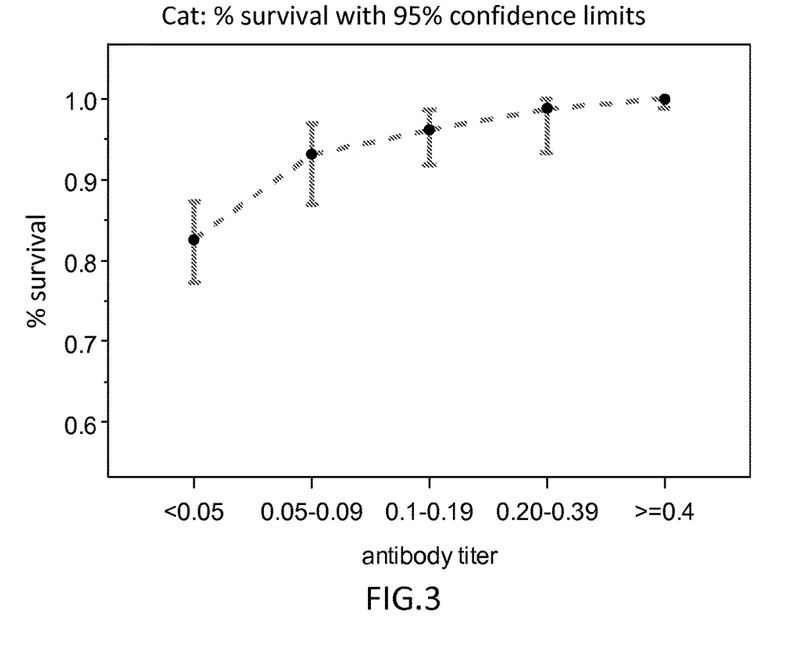
FIG. 3 is a graph analyzing the survival rate of cats at various antibody titer levels with 95% confidence limits.

The results of this analysis for cats is shown in the Table below, as well as in FIG. 3.

TABLE 9

Comparison of Cat Survival Rates

| titer | % survival | lcl_95 | ucl_95 |
|---|---|---|---|
| <0.05 | 82.6% | 77.3% | 87.2% |
| 0.05-0.09 | 93.1% | 86.9% | 97.0% |
| 0.1-0.19 | 96.2% | 91.8% | 98.6% |
| 0.20-0.39 | 98.8% | 93.4% | 100% |
| >=0.4 | 100% | 98.9% | 100% |

The comparison of survival rate at <0.5 and ≥0.5 threshold were conducted based on the CMH statistic in the exact test. P-values were all <0.0001. Exact 95% confidence limits for the survival rate were computed at each titer level. The 95% confidence interval of odds ratio was estimated using the exact method. Results of this analysis are shown in the Table below.

TABLE 10

| | Titer | % Survival | 95% Lower limit | 95% Upper limit | Odds Ratio |
|---|---|---|---|---|---|
| Dog | ≥0.5 | 100% | 99.1% | 100% | (24.40, ∞) |
| | <0.5 | 84.4% | 82.4% | 86.3% | |
| Cat | ≥0.5 | 100% | 99.0% | 100% | (12.03, ∞) |
| | <0.5 | 90.4% | 87.8% | 92.7% | |

If one were to consider the risk of cats with a known rabies antibody titer above 0.5 IU/ml, this risk of infection drops to only 1 animal in 50,000. The decrease in risk for dogs above 0.5 IU/mL is even more dramatic; only 1 in 1.68 million dogs would succumb to the same challenge. Not only would allowing titers to be used in lieu of routine vaccination given pet owners an aid in avoiding the adverse reaction to vaccination but it would truly be safer in terms of infection risk if the threshold were set at 0.5 IU/mL.

These conclusions mean that we can recommend rabies vaccination boosters (as we do for humans) on an individual and appropriate basis, just as recommended for all other core vaccinations. Although a titer of 0.5 IU/mL is very nearly always protective in the face of a massive challenge, if an exposure to rabies does occur, it is recommended that a booster always be taken. Implementation of accepting antibody titers can be as simple as allowing local pet licensure agencies to accept either current vaccination against rabies or a rabies antibody titer above 0.5 IU/mL run by a qualified method.

Example 3

Illustrative Detection of Rabies Antibody

Described herein is the semi-quantitative detection of antibodies against rabies. A detection strip made of nitrocellulose that is flanked at one end by a reagent pad that contains dried colloidal gold-labeled anti-viral IgG detector antibody(ies) and at the other end by an absorption pad. The detector antibody(ies) would be directed against viral epitopes which have been previously shown to cause viral neutralization. Utilizing a detector (labelled) antibody against the glycoprotein (which all neutralizing antibodies target), we will be able to give an accurate screen for neutralizing antibodies in a rapid, point-of-care platform.

A sample application pad would flank the reagent pad. Heat-resistant antigens will be prepared from viral strains by boiling of a washed and concentrated viral culture. The boiled suspension is centrifuged to remove cell debris, and the supernatant containing the antigen is filtered. The antigen(s) of interest along with a soluble dye viewable in the visible spectrum will be deposited as a narrow line(s) onto the nitrocellulose strip in the detection region. Staph A (*staphylococcus*-derived Protein A), a bacterial protein that non-specifically binds IgG, is included and deposited as a separate narrow line to bind excess detector (labelled) antibodies and function as a reagent control. The composite will be backed by a support and cut into test strips to fit a (plastic) housing. The housing comprises a sample application opening positioned above the sample application pad and a detection window positioned above the detection region. Two intersecting test strips can be used in some embodiments, with the test strips intersecting or overlapping at the detection region. The amounts of antigen and detection reagent will be optimized in a step-by-step procedure with a panel of positive and negative control sera. In general, an amount of antigen will be immobilized on the test region that is capable of binding to an amount of rabies antibody corresponding to a minimum immunoprotective level of the rabies antibody (e.g., 0.5 IU/mL).

The assay will be performed by the addition of the patient's sample (e.g., whole blood, serum, etc.) along with sample buffer added simultaneously or sequentially with the patient sample to the test strip. The buffer facilitates the flow of the sample along the test strip and over the antigen test lines in the detection region. The completion of this first step can be visually determined as the dye is solubilized and moved away from the antigen test lines in the detection region. Following completion of the dye's disappearance, the assay proceeds to the second step. In a second step, detector antibodies will be flowed across the antigen test lines. Detector antibodies will be labelled with a visually discernible color (e.g., dye). When using a dual path system, this is accomplished by addition of a second buffer containing the detector antibodies to a second opening above a second test strip that intersects with the first test strip above. The second buffer flows along the second test strip and intersects with the antigen test lines.

Regardless, if the test sample (animal blood) has a minimum immunoprotective level of the rabies antibody to the target antigen, the antigenic site(s) in the test line(s) will be substantially and preferably completely blocked (by the patient's sample). The detector antibodies will pass over the antigen line without a visible line developing, indicating adequate protection for rabies (i.e., a titer of at least 0.5 IU/mL). A test sample with an inadequate immunoprotective level of rabies antibodies will be indicated when the detector antibodies react with unblocked sites on the antigen test line(s) creating a visible line. Appearance of a line will indicate a need for vaccination or booster for rabies. Test results will be considered valid when excess detector (labelled) antibodies are bound by the line containing Staph A protein, resulting in a (secondary) visual band.

Multiple different antigens can be screened in one test by using different antigen lines for each target. The position of each specific antigen can be marked on the device.

We claim:

1. A method of determining the necessity of re-vaccination of an animal against at least one pathogen, said method comprising:
    (a) contacting a test sample from said animal with a test article, said test article comprising:
        a first elongated solid support having a top surface, said top surface comprising:
            a sample application region and a detection region, said sample application region being in capillary flow communication with said detection region and having a first path of flow therebetween, wherein said detection region comprises:
                first immobilized antigen and a soluble dye in a first defined area of said detection region, wherein said immobilized antigen specifically binds a minimum immunoprotective level of antibody to said at least one pathogen; and
                a control compound in a second defined area of said detection region, said first defined area being distinct from said second defined area; and
            a second elongated solid support, said second solid support intersecting said first solid support at said detection region, said second solid support comprising a top surface comprising a reporter application region being in capillary flow communication with said detection region and having a second path of flow therebetween, wherein said reporter application region comprises dried reporter antibodies removably affixed thereto, said reporter antibodies labelled to generate a detectable signal;
            wherein said test sample is deposited on said sample application region, said sample flowing by capillary action to said detection region along said first path of flow;
    (b) observing said detection region for disappearance of said soluble dye from said first defined area of said detection region;
    (c) after disappearance of said soluble dye, contacting said detection region with said reporter antibodies by depositing buffer solution onto said reporter application region, said buffer solution initiating flow of said reporter antibodies from said reporter application region to said detection region by capillary action along said second path of flow, wherein said reporter antibodies are configured to selectively bind said first immobilized antigen and non-selectively bind said control compound; and
    (d) observing said detection region for changes, said changes comprising: appearance of a detectable signal in said second defined area as a positive control, and appearance of a detectable signal in said first defined region, wherein appearance of a detectable signal in both said first and second defined areas indicates that said animal does not have said minimum immunoprotective level of antibody to said at least one pathogen such that there is a need for re-vaccination of said animal, and wherein appearance of a detectable signal only in said second defined area indicates that said animal has said minimum immunoprotective level of antibody to said at least one pathogen such that there is no necessity for re-vaccination of said animal.

2. The method of claim 1, wherein said elongated solid support top surface comprises a porous membrane or matrix, said solid support further comprising a fluid impervious layer adjacent said porous membrane or matrix.

3. The method of claim 2, wherein said sample application region comprises an absorbent pad.

4. The method of claim 1, wherein said animal is a canine and said pathogen is rabies, said minimum immunoprotective level of antibody being 0.5 IU/mL.

5. The method of claim 1, wherein said first immobilized antigen is whole killed virus bound to said first defined area.

6. The method of claim 1, wherein said control compound is a bacterial protein that non-specifically binds said reporter antibodies.

7. The method of claim 1, wherein reporter antibodies compete against neutralizing antibodies for binding to said antigen.

8. The method of claim 1, said test article further comprising a cassette or housing, said first elongated solid support being retained in said housing, said housing comprising an opening above said sample application region configured for receiving test sample deposited onto said sample application pad through said opening.

9. The method of claim 8, said housing further comprising an opening above said detection region configured for viewing changes in said detection region.

10. The method of claim 1, wherein said detectable signal is a color viewable in the visible spectrum.

11. The method of claim 10, wherein said detectable signal appears as a visually discernable line or dot in said first or second defined areas.

12. The method of claim 1, wherein said test sample comprises blood, serum, or plasma from said animal mixed with buffer.

13. The method of claim 12, further comprising collecting said blood, serum, or plasma from said animal immediately prior to contacting said test sample with said test article.

14. The method of claim 13, wherein said observing (d) can be carried out in less than about 20 minutes after said collecting.

15. The method of claim 1, wherein said observing (b) occurs less than about 5 minutes after said contacting (a).

16. The method of claim 1, wherein said observing (d) occurs less than about 5 minutes after said contacting (c).

17. A test article for determining the necessity of re-vaccination of an animal against at least one pathogen, said article comprising:
a first elongated solid support having a top surface, said top surface comprising:
a sample application region and a detection region, said sample application region being in capillary flow communication with said detection region and having a first path of flow therebetween, wherein said detection region comprises:
first immobilized antigen and a soluble dye in a first defined area of said detection region, wherein said immobilized antigen specifically binds a minimum immunoprotective level of antibody to said at least one pathogen; and
a control compound in a second defined area of said detection region, said first defined area being distinct from said second defined area;
a second elongated solid support, said second solid support intersecting said first solid support at said detection region, said second solid support comprising a top surface, said top surface comprising a reporter application region being in capillary flow communication with said detection region and having a second path of flow therebetween, wherein said reporter application region comprises dried reporter antibodies removably affixed thereto, said reporter antibodies being labelled to generate a detectable signal, wherein said reporter antibodies are configured to selectively bind said first immobilized antigen and non-selectively bind said control compound.

18. The article of claim 17, wherein said labelled reporter antibodies compete against neutralizing antibodies for binding said first immobilized antigen.

19. The article of claim 17, wherein said elongated solid support top surface comprises a porous membrane or matrix, said solid support further comprising a fluid impervious layer adjacent said porous membrane or matrix.

20. The article of claim 17, wherein said sample application region comprises an absorbent pad.

21. The article of claim 17, wherein said animal is a canine and said pathogen is rabies, said minimum immunoprotective level of antibody being 0.5 IU/mL.

22. The article of claim 17, wherein said pathogen is a virus, and said immobilized antigen is whole killed virus bound to said first defined area.

23. The article of claim 17, said test article further comprising a housing, said first elongated solid support and second elongated support being retained in said housing, said housing comprising an opening above said sample application region configured for receiving test sample deposited onto said sample application region through said opening, and an opening above said reporter application region configured for receiving buffer or reporter antibodies deposited onto said reporter application region through said opening.

24. The article of claim 23, said housing further comprising an opening above said detection region configured for viewing changes in said detection region.

25. The article of claim 24, wherein said opening comprises a clear window through which said changes are visible.

26. The article of claim 17, wherein said first immobilized antigen and soluble dye are arranged as a line or dot defining said first defined area.

27. The article of claim 17, wherein said control compound is arranged as a line or dot defining said second defined area.

28. The article of claim 17, said first solid support further comprising second immobilized antigen in a third defined area of said detection region, said third defined area being distinct from said first and second defined areas, said second immobilized antigen being different from said first immobilized antigen, wherein said second immobilized antigen specifically binds a minimum immunoprotective level of antibody to a second pathogen that is different from said at least one pathogen.

29. A kit for point-of-care determination of the necessity of re-vaccination of an animal against a pathogen, said kit comprising:
a test article according to claim 17;
optional reagents or buffers; and
instructions for collecting a test sample from said animal and testing said test sample using said test article to determine if said animal has a minimum immunoprotective level of antibody against said pathogen such that there is no necessity for re-vaccination of said animal.

30. The kit of claim 29, wherein said animal is a canine and said pathogen is rabies, said minimum immunoprotective level of antibody being 0.5 IU/mL.

* * * * *